US010293012B2

(12) United States Patent
Langland et al.

(10) Patent No.: US 10,293,012 B2
(45) Date of Patent: May 21, 2019

(54) METHODS OF USING EXTRACTS OF MELISSA OFFICINALIS AGAINST FILOVIRUSES

(71) Applicants: Jeffrey Langland, Chandler, AZ (US); Bertram Jacobs, Tempe, AZ (US); Karen Denzler, Phoenix, AZ (US)

(72) Inventors: Jeffrey Langland, Chandler, AZ (US); Bertram Jacobs, Tempe, AZ (US); Karen Denzler, Phoenix, AZ (US)

(73) Assignee: Arizona Board of Regents on behalf of Arizona State University, Scotsdale, AZ (US)

( * ) Notice: Subject to any disclaimer, the term of this patent is extended or adjusted under 35 U.S.C. 154(b) by 0 days.

(21) Appl. No.: 15/970,222

(22) Filed: May 3, 2018

(65) Prior Publication Data

US 2018/0318373 A1 Nov. 8, 2018

Related U.S. Application Data

(60) Provisional application No. 62/501,446, filed on May 4, 2017.

(51) Int. Cl.
*A61K 36/53* (2006.01)
*A61P 31/14* (2006.01)

(52) U.S. Cl.
CPC .............. *A61K 36/53* (2013.01); *A61P 31/14* (2018.01); *A61K 2236/333* (2013.01)

(58) Field of Classification Search
None
See application file for complete search history.

(56) References Cited

U.S. PATENT DOCUMENTS

| | | | |
|---|---|---|---|
| 2005/0095260 | A1 | 5/2005 | Pardoe |
| 2007/0122492 | A1 | 5/2007 | Behr et al. |
| 2012/0141610 | A1 | 6/2012 | Gowey |
| 2018/0200320 | A1 | 7/2018 | Langland et al. |

FOREIGN PATENT DOCUMENTS

| | | | |
|---|---|---|---|
| EP | 0249165 | A2 | 12/1987 |
| WO | 2005074947 | A2 | 8/2005 |
| WO | 2009048595 | A2 | 4/2009 |
| WO | 2014081976 | A1 | 5/2014 |
| WO | 2016012913 | A1 | 1/2016 |
| WO | 2016123223 | A1 | 8/2016 |
| WO | 2018208739 | A1 | 11/2018 |

OTHER PUBLICATIONS

Chattopadhyay, et al., Evidence-Based Validation of Herbal Medicine, Ch.8:175. (Year: 2015).*

Arndt, W. et al., "In Vitro Characterization of a Nineteenth-Century Therapy for Smallpox", PLoS One, Mar. 2012, 7(3), article ID e23610, 9 pages.

Astani, A. et al., "Melissa officinalis Extract Inhibits Attachment of Herpes Simplex Virus in vitro", Chemotherapy, 2012 (published online Feb. 2012), 58, pp. 70-77.

Chattopadhyay, D. et al., "Ethnomedicines and ethnomedicinal phytophores against herpesviruses", Biotechnology Annual Review, 2008 (available online Jul. 2008), 14, pp. 297-348.

Cheng, C. et al., "Recent Advances in the Discovery of Novel Anti-Herpetic Agents from Chinese Herbal Medicines", Current Organic Chemistry, 2010, 14(16), pp. 1714-1726.

Downing, A., "Inter and intra-specific differences in medicinal plant use for the treatment of type II diabetes symptoms by the Cree Elders of Eeyou Istchee (QC)", University of Montreal, Papyrus Institutional Repository, Master's Thesis, 2010, 117 pages.

Harris, C. et al., "Characterizing the cytoprotective activity of *Sarracenia purpurea* L., a medicinal plant that inhibits glucotoxicity in PC12 cells", BMC Complementary and Alternative Medicine, Dec 2012, 245, 10 pages, https://doi.org/10.1186/1472-6882-12-245.

Krauze-Baranowska, A. et al., "HPLC of flavanones and chalcones in different species and clones of Sali", Acta Poloniae Pharmaceutica, Jan. 2013, 70(1), pp. 27-34.

Patent Cooperation Treaty, International Searching Authority, International Preliminary Report on Patentability and Written Opinion for PCT/US2013/071332, 12 pages, report dated May 26, 2015, opinion dated Apr. 30, 2014.

Patent Cooperation Treaty, International Searching Authority, International Search Report for PCT/US2013/071332, 6 pages, dated Apr. 30, 2014.

Patent Cooperation Treaty, International Searching Authority, International Search Report for PCT/US2018/031538, 4 pages, dated Sep. 17, 2018.

Patent Cooperation Treaty, International Searching Authority, Written Opinion for PCT/US2018/031538, 7 pages, dated Sep. 17, 2018.

Perfect, M. et al., "Use of Complementary and Alternative Medicine for the Treatment of Genital Herpes", Herpes, Oct. 2005, 12(2), pp. 38-41.

Salvador, B. et al., "Filoviruses Utilize Glycosaminoglycans for Their Attachment to Target Cells", Journal of Virology, Mar. 2013 (published ahead of print Jan. 2013), 87(6), pp. 3295-3304.

USPTO, Non-Final Office Action for U.S. Appl. No. 14/443,767, dated Aug. 1, 2018, 8 pages.

Wang, Z. et al., "High Genetic Diversity in *Sarracenia leucophylla*(Sarraceniaceae), a Carnivorous Wetland Herb", Journal of Heredity, May 2004, 95(3), pp. 234-243.

* cited by examiner

*Primary Examiner* — Michael Barker

(74) *Attorney, Agent, or Firm* — Byrne Poh LLP; Nina R. Horan

(57) ABSTRACT

The present disclosure relates to methods of using *Melissa officinalis* extracts in inhibiting viral replication of a filovirus and in treating or preventing a filovirus infection.

19 Claims, 8 Drawing Sheets

*Melissa officinalis*

METHODS OF USING EXTRACTS OF MELISSA OFFICINALIS AGAINST FILOVIRUSES

BACKGROUND

Medicinal plant extracts are of interest as sources of novel antiviral agents. *Melissa officinalis*, commonly known as Lemon Balm, is an abundant botanical historically claimed to have strong antiviral properties. Melissa has a long medicinal history being used first up to two thousand years ago by the Greeks. Melissa is purported to help significantly in the treatment of herpes simplex viruses, HSV1 and HSV2.

The antiviral activity associated with Melissa has utilized glycerine-based extracts prepared from dried *Melissa officinalis*. The botanical was ground to a fine powder followed by resuspension in 75% glycerin (pharmaceutical grade, organic vegetable glycerin) at a ratio of 1:8 (dried plant material to extraction solution). The solution was stored at room temperature for seven days followed by removal of the botanical debris by centrifugation and sterilization through a 0.2 um filter.

Previous studies have demonstrated that extracts from *Melissa officinalis* can inhibit the replication of herpes viruses. As shown in FIG. 1 (lower left corner), cells infected with HSV lead to dramatic cytopathic effects and cell death. As cells were treated with increasing concentrations of Melissa extract, a dose dependent reduction in cell death was observed. Uninfected cells (FIG. 1, upper row) remained morphologically normal and healthy.

Many different cell surface molecules can serve as receptors for the attachment and entry of viruses. The particular receptor or receptors a virus can use will determine the cell types it can infect. For HSV1, cell surface heparin sulfate proteoglycans serve as the cell surface receptor. Previous data demonstrates that cells treated with heparinases or altered by mutations that prevent heparin sulfate biosynthesis have reduced capabilities to bind HSV1 and are partially resistant to virus infection. Soluble heparin has been shown to competitively inhibit HSV1 infection. Through temporal studies, it has been demonstrated that extracts of Melissa can inhibit HSV1 binding to cells. In support of this, since herpes viruses are known to bind to cells utilizing heparin sulfate proteoglycans, the ability of the Melissa extract to competitively inhibit herpes virus binding to a heparin-agarose resin was tested. As shown in FIG. 2, the Melissa extract blocked herpes virus binding to the resin as detected by a decrease in the viral glycoprotein B (gB). These and previous results suggest that Melissa acts by inhibiting herpes virus cellular attachment.

Blocking HSV1 attachment to cells could occur by components in Melissa either binding directly to the virus or by binding to the cell. As shown in FIG. 3, when cells were preincubated with the extract, washed and then infected with HSV1, virus replication was not inhibited. However, if the extract was preincubated with purified HSV1 virions, which were then washed and tested for infectivity, virus replication was inhibited (FIG. 3). These results support that the active constituent(s) in the Melissa extract bind to the herpes virion and inhibit viral attachment to the cell. The HSV1 glycoprotein B (gB) is one of the major viral surface proteins involved in binding the virus to heparin sulfate proteoglycans on the cell surface. Since Melissa components bind to the virus and inhibit binding to the cellular heparin sulfate proteoglycan, the HSV1 gB is a likely target for Melissa interaction. In support of this, the Melissa extract was depleted of gB-binding components by affinity chromatography. After removal of gB binding components present in the Melissa extract, the HSV1 inhibitory activity was greatly reduced (FIG. 4). This result suggests that the active constituent of Melissa binds to gB of the virion particle. In summary, these results support that Melissa extracts inhibit herpes virus binding to heparin sulfate on the cell surface by binding to the HSV1 gB and blocking viral attachment.

Cell cytotoxicity is an important concern when considering any potential therapeutic. In assays, inhibition of HSV1 virus replication occurred at a low dose ($EC_{50}$=0.58 ul/ml) (FIG. 5). Upon testing for cell cytotoxicity, the extract did not exhibit detectable cell cytotoxicity with the $CC_{50}$=190 ul/ml being comparable to glycerin (vehicle) alone. (FIG. 5).

SUMMARY

The present disclosure relates to the discovery that extracts of the botanical *Melissa officinalis* have antiviral activity against filoviruses. Accordingly, the present disclosure provides a method of using *Melissa officinalis* extracts in inhibiting viral replication of a filovirus. The present disclosure also provides a method of using *Melissa officinalis* extracts in treating or preventing a filovirus infection.

In one embodiment, the filovirus is an Ebola virus. In another embodiment, the filovirus is Marburg virus.

BRIEF DESCRIPTION OF THE FIGURES

FIG. 6 shows that Melissa potently inhibits replication of HSV1, HSV2 and Ebola-VSV, moderately inhibits replication of VACV, SV40 and Adenovirus, poorly inhibits replication of VSV and does not inhibit replication of Reovirus or EMCV.

FIG. 7 shows a repeat of Ebola-VSV assay.

FIG. 8A and FIG. 8B show that neither *Hypericum* nor *Lavandula* specifically inhibit replication of Ebola-VSV.

DETAILED DESCRIPTION

Figure 1:
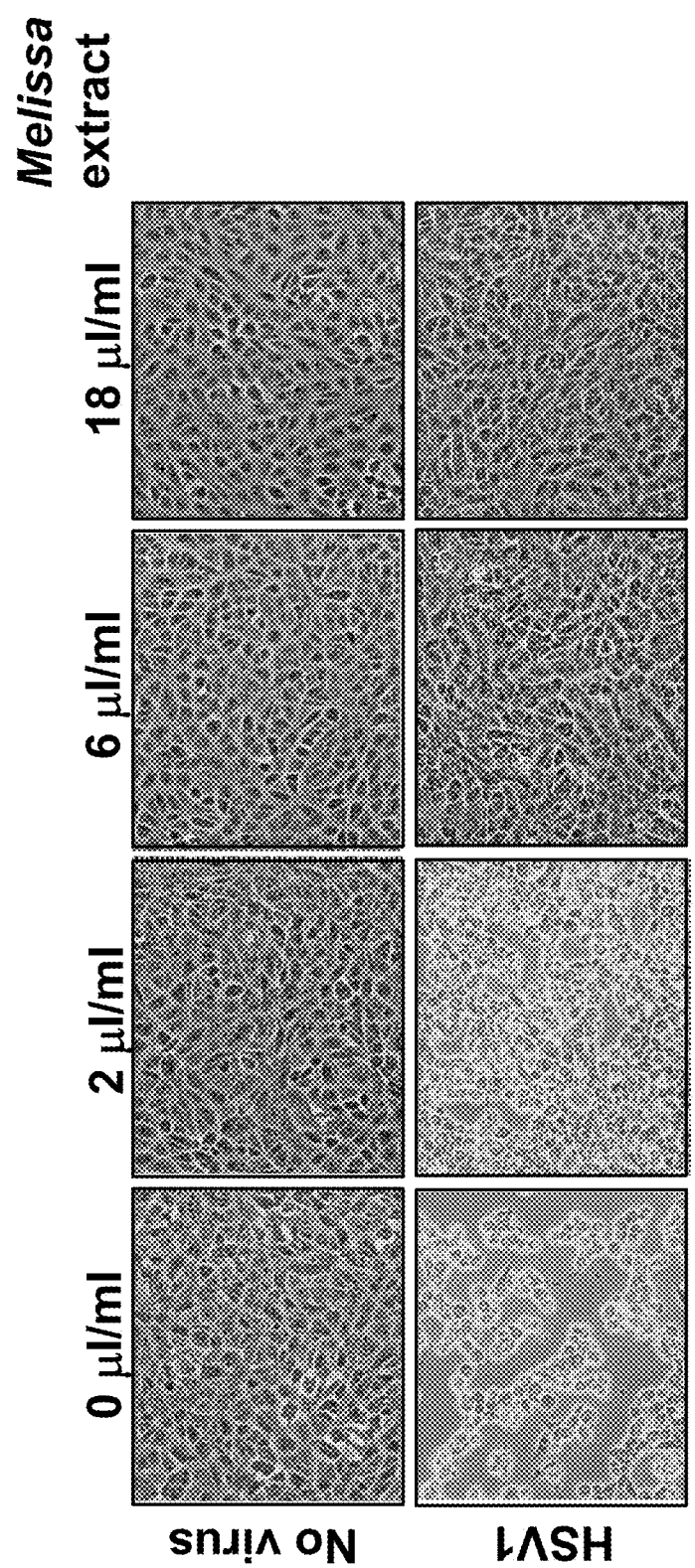
FIG. 1 shows that Melissa inhibits replication of HSV1.
Figure 2:
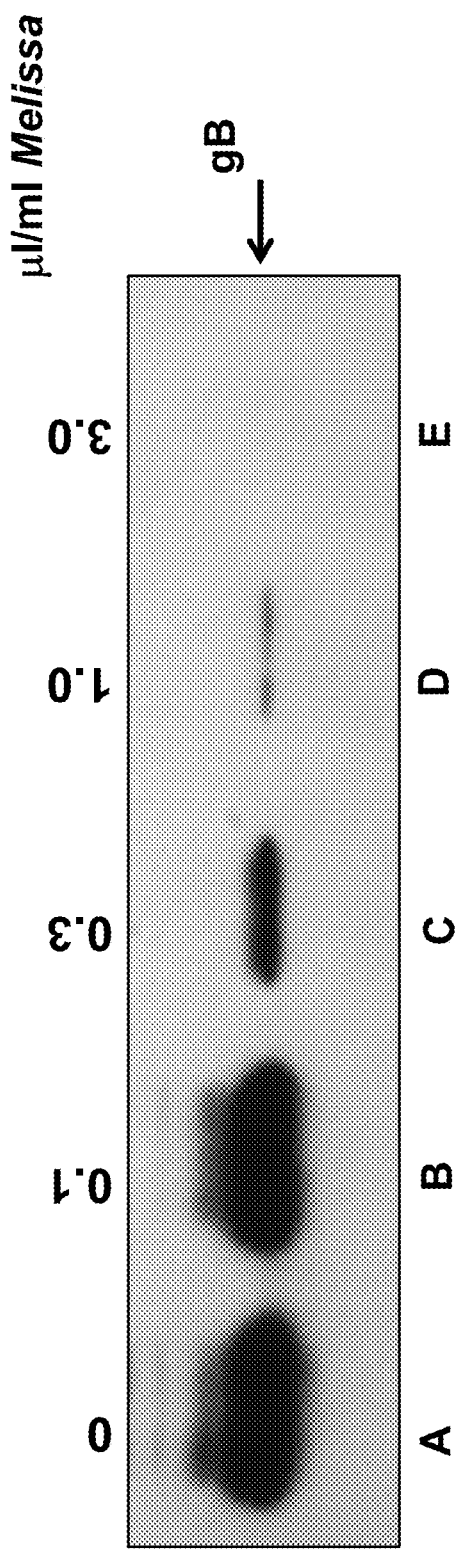
FIG. 2 shows that Melissa inhibits binding of HSV to heparin agarose, at a dose similar to which it inhibits replication of HSV.
Figure 3:
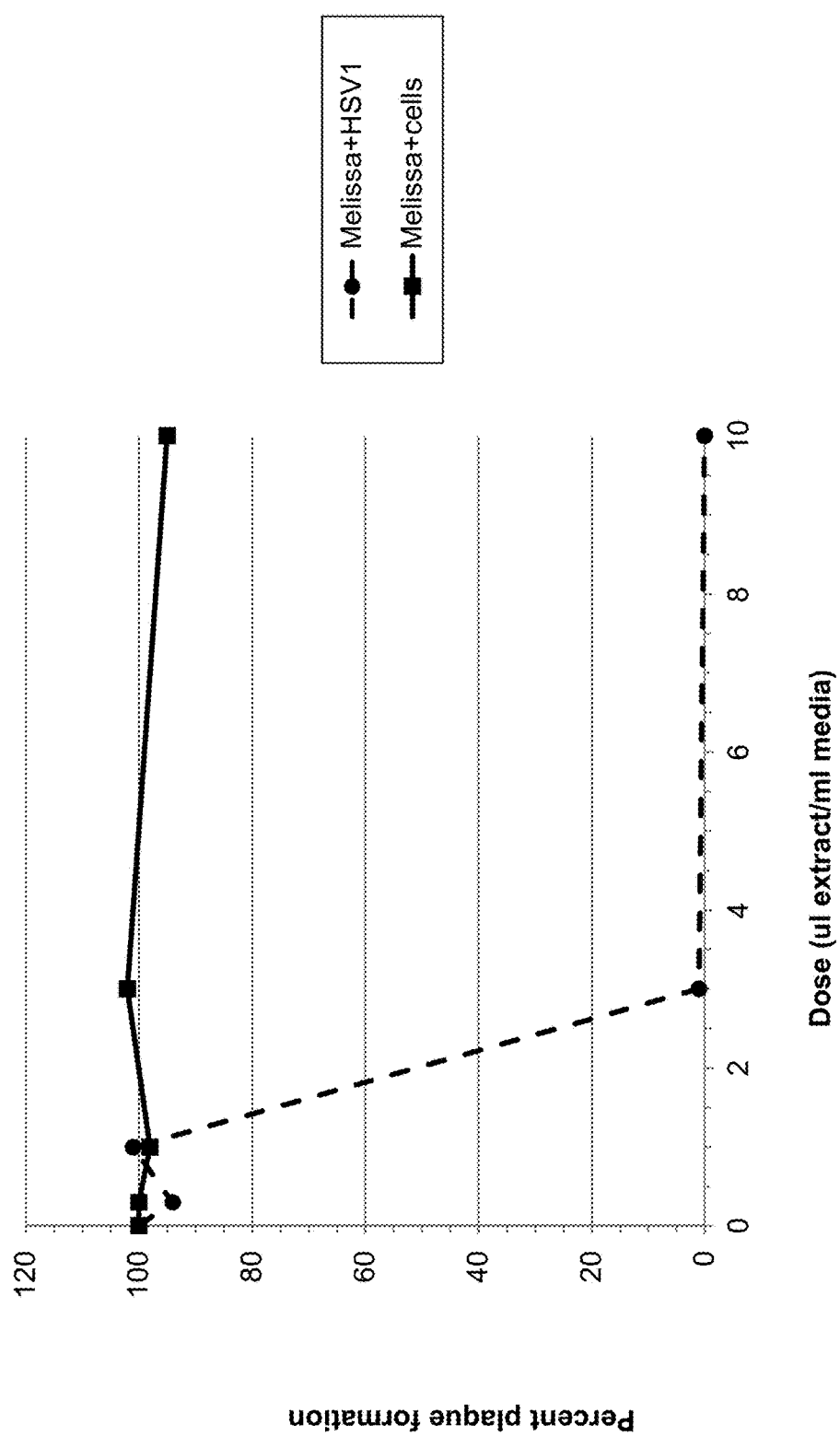
FIG. 3 shows that Melissa inhibits HSV1 replication when added to the virus, but not when added to cells
Figure 4:
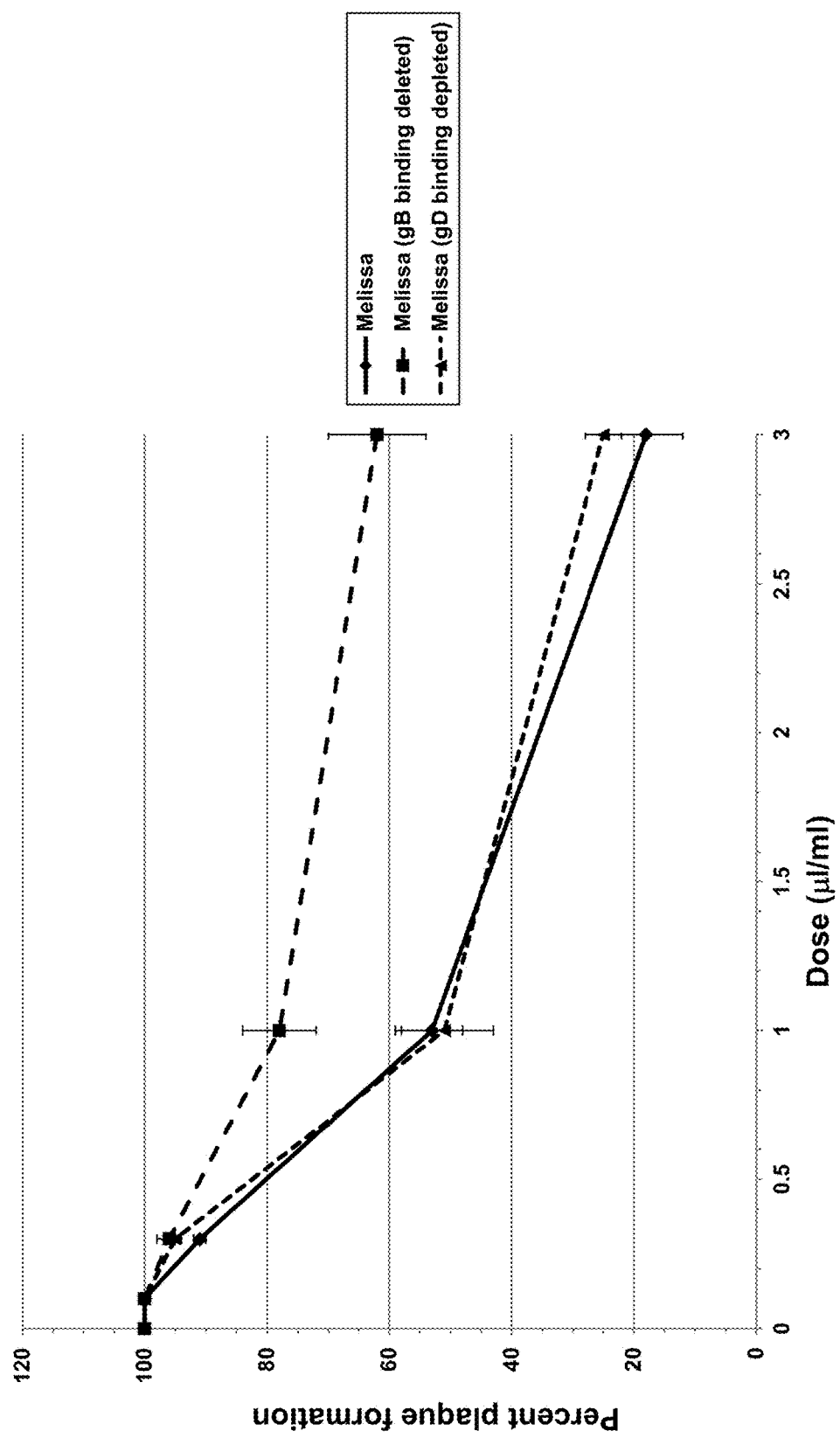
FIG. 4 shows that anti-HSV1 components in Melissa likely bind to the viral glycoprotein B.
Figure 5:
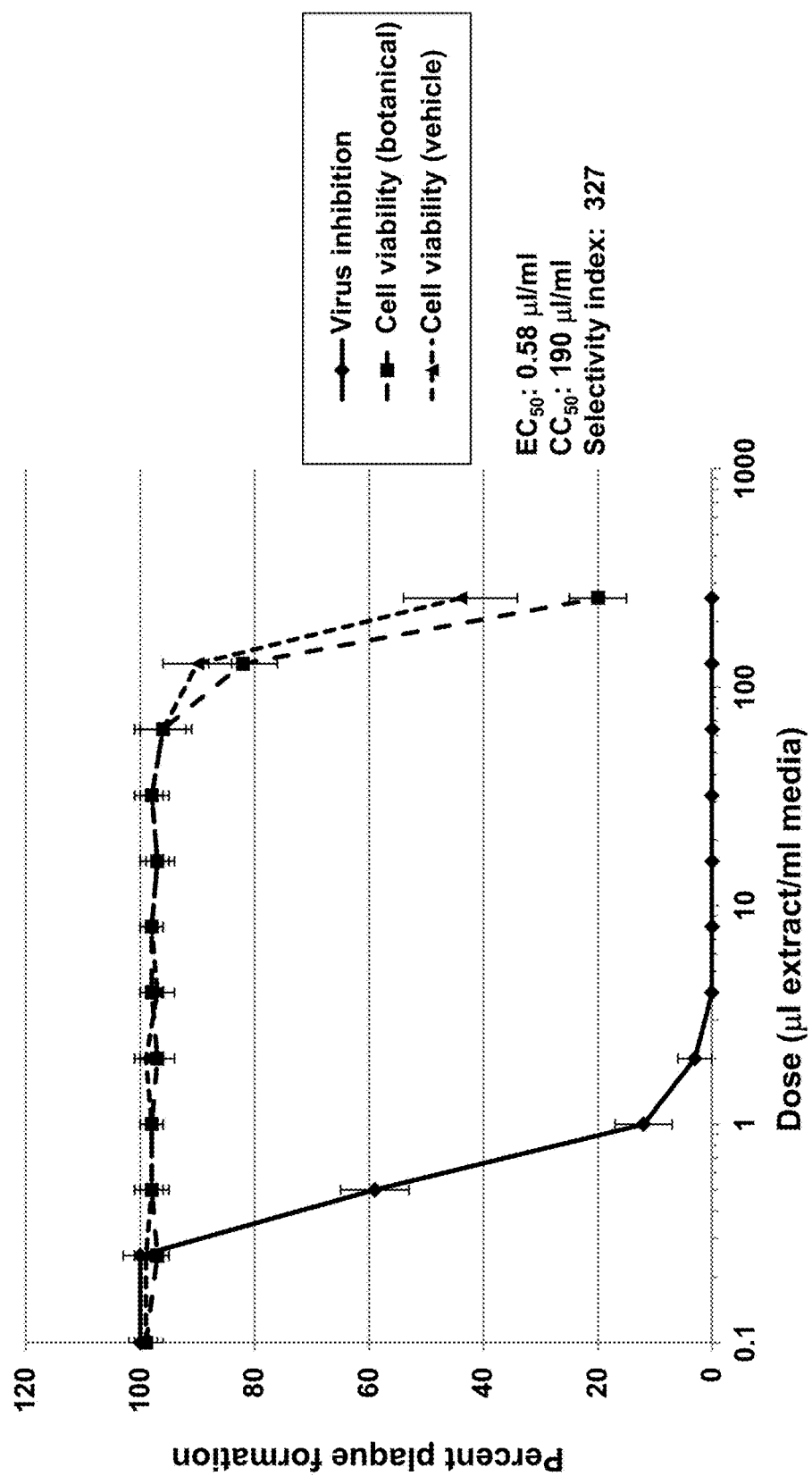
FIG. 5 shows that Melissa has very low toxicity to uninfected cells.

The disclosure includes the following:
1. A method of inhibiting viral replication of a filovirus, the method comprising exposing the filovirus or a filovirus-infected cell to an effective amount of an extract from a plant in the Lamiaceae family, or a composition comprising the extract, wherein the exposing inhibits viral replication within the cell.
2. A method of treating filovirus infection of a cell, the method comprising exposing a filovirus or filovirus-infected cell to an effective amount of an extract from a plant in the Lamiaceae family, or a composition comprising the extract, wherein the exposing inhibits the entry of the filovirus into the cell.
3. A method of preventing filovirus infection of a cell, the method comprising exposing the cell to an effective amount of an extract from a plant in the Lamiaceae family, or a composition comprising the extract, prior to exposure of the cell to the filovirus, wherein the exposing the cell to the *Melissa officinalis* extract, or a composition comprising *Melissa officinalis* extract inhibits filovirus infection.

4. A method of inhibiting viral replication of a filovirus, the method comprising exposing the filovirus or a filovirus-infected cell to an effective amount of *Melissa officinalis* extract, or a composition comprising *Melissa officinalis* extract, wherein the exposing inhibits viral replication within the cell.

5. A method of treating filovirus infection of a cell, the method comprising exposing a filovirus or filovirus-infected cell to an effective amount of *Melissa officinalis* extract, or a composition comprising *Melissa officinalis* extract, wherein the exposing inhibits the entry of the filovirus into the cell.

6. A method of preventing filovirus infection of a cell, the method comprising exposing the cell to an effective amount of *Melissa officinalis* extract, or a composition comprising *Melissa officinalis* extract, prior to exposure of the cell to the filovirus, wherein the exposing the cell to the *Melissa officinalis* extract, or a composition comprising *Melissa officinalis* extract inhibits filovirus infection.

7. The method of any one of the above, wherein the cell is a human cell.

8. A method of treating a subject infected with filovirus, the method comprising administering an effective amount of an extract from a plant in the Lamiaceae family, or a composition comprising the extract, to the subject, thereby treating the subject infected with filovirus.

9. A method of preventing infection of a subject with filovirus, the method comprising administering an effective amount of an extract from a plant in the Lamiaceae family, or a composition comprising the extract, to the subject prior to exposure of the subject to filovirus, thereby preventing infection with filovirus.

10. A method of treating a subject infected with filovirus, the method comprising administering an effective amount of *Melissa officinalis* extract, or a composition comprising *Melissa officinalis* extract, to the subject, thereby treating the subject infected with filovirus.

11. A method of preventing infection of a subject with filovirus, the method comprising administering an effective amount of *Melissa officinalis* extract, or a composition comprising *Melissa officinalis* extract, to the subject prior to exposure of the subject to filovirus, thereby preventing infection with filovirus.

12. The method of any of the above, wherein the filovirus is an Ebola virus.

13. The method of any of the above 1-11, wherein the filovirus is Marburg virus.

14. The method of any of the above, wherein the *Melissa officinalis* extract comprises dried plant material and extraction solution.

15. The method of any of the above 1-13, wherein the *Melissa officinalis* extract comprises fresh plant material and extraction solution.

16. The method of the above 14 or 15, wherein the extraction solution comprises water.

17. The method of the above 16, wherein the extraction solution further comprises glycerin.

18. The method of the above 17, wherein the extraction solution comprises glycerin in an amount ranging from about 0.01% to about 90%.

19. The method of the above 17, wherein the extraction solution comprises glycerin in an amount ranging from about 50% to about 85%.

20. The method of the above 17, wherein the extraction solution comprises glycerin in an amount ranging from about 65% to about 80%.

21. The method of the above 16, wherein the extraction solution further comprises ethanol.

22. The method of the above 21, wherein the extraction solution comprises ethanol in an amount ranging from about 0.01% to about 30%.

23. The method of the above 21, wherein the extraction solution comprises ethanol in an amount ranging from about 10% to about 25%.

24. The method of the above 21, wherein the extraction solution comprises ethanol in an amount ranging from about 15% to about 20%.

25. The method of any of the above 14 or 16-24, wherein the *Melissa officinalis* extract comprises dried plant material and extraction solution and the ratio between the dried plant material and the extraction solution is from about 1:3 to about 1:15.

26. The method of the above 25, wherein the ratio between the dried plant material and the extraction solution present in the *Melissa officinalis* extract is from about 1:6 to about 1:12.

27. The method of the above 25, wherein the ratio between the dried plant material and the extraction solution present in the *Melissa officinalis* extract is from about 1:7 to about 1.10.

28. The method of any of the above 15-24, wherein the *Melissa officinalis* extract comprises fresh plant material and extraction solution and the ratio between the fresh plant material and the extraction solution is from about 1:3 to about 1:15.

29. The method of the above 28, wherein the ratio between the fresh plant material and the extraction solution present in the *Melissa officinalis* extract is from about 1:6 to about 1:12.

30. The method of the above 28, wherein the ratio between the fresh plant material and the extraction solution present in the *Melissa officinalis* extract is from about 1.7 to about 1.10.

31. The method of any of the above 8-30, further comprising administering an additional therapeutic agent.

DEFINITIONS

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "effective amount" refers to an amount of an extract of the disclosure effective to treat a disease or disorder in a subject.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state. Those in need of treatment include those already having the condition or disorder as well as those prone to have the condition or disorder.

The term "subject" as used herein, includes, but is not limited to, a human, rat, mouse, guinea pig, monkey, pig, goat, cow, horse, dog, cat, bird and fowl. In some embodiments, the subject is a human.

Methods of Use

The present disclosure provides methods of using an extract from a plant in the Lamiaceae family, or a composition comprising the extract. The extracts are useful for inhibiting viral replication of a filovirus and in treating or preventing an infection by a filovirus.

In one particular embodiment, the present disclosure provides a method of inhibiting viral replication of a filovirus. The method comprises exposing the filovirus or a filovirus-infected cell to an effective amount of an extract from a plant in the Lamiaceae family, or a composition comprising the extract. The step of exposing the filovirus or filovirus-infected cell to the extract inhibits viral replication within the cell.

In another particular embodiment, the present disclosure provides a method of treating filovirus infection of a cell. The method comprises exposing a filovirus or filovirus-infected cell to an effective amount of an extract from a plant in the Lamiaceae family, or a composition comprising the extract. The step of exposing the filovirus or filovirus-infected cell to the extract inhibits the entry of the filovirus into the cell.

In another particular embodiment, the present disclosure provides a method of preventing filovirus infection of a cell. The method comprises exposing the cell to an effective amount of an extract from a plant in the Lamiaceae family, or a composition comprising the extract, prior to exposure of the cell to the filovirus. The step of exposing the cell to the *Melissa officinalis* extract, or a composition comprising *Melissa officinalis* extract inhibits filovirus infection.

In another particular embodiment, the present disclosure provides a method of treating a subject infected with filovirus. The method comprises administering an effective amount of an extract from a plant in the Lamiaceae family, or a composition comprising the extract, to the subject, thereby treating the subject infected with filovirus.

In another particular embodiment, the present disclosure provides a method of preventing infection of a subject with filovirus. The method comprises administering an effective amount of an extract from a plant in the Lamiaceae family, or a composition comprising the extract, to the subject prior to exposure of the subject to filovirus, thereby preventing infection with filovirus.

Examples of plants from the Lamiaceae family that can be used in the methods of the present disclosure include *Acanthomintha, Achyrospermum, Acinos, Acrocephalus, Acrotome, Acrymia, Adelosa, Aegiphila, Aeollanthus, Agastache, Ajuga, Ajugoides, Alajja, Alvesia, Amasonia, Amethystea, Anisochilus, Anisomeles, Archboldia, Asterohyptis, Ballota, Basilicum, Becium, Benguellia, Blephilia, Bostrychanthera, Bovonia, Brachysola, Brazoria, Bystropogon, Calamintha, Callicarpa, Capitanopsis, Capitanya, Caryopteris, Catoferia, Cedronella, Ceratanthus, Chaiturus, Chamaesphacos, Chaunostoma, Chelonopsis, Chloanthes, Cleonia, Clerodendrum, Clinopodium, Colebrookea, Collinsonia, Colquhounia, Comanthosphace, Congea, Conradina, Coridothymus, Cornutia, Craniotome, Cryphia, Cuminia, Cunila, Cyanostegia, Cyclotrichium, Cymaria, Dauphinea, Dicerandra, Dicrastylis, Discretitheca, Dorystoechas, Dracocephalum, Drepanocaryum, Elsholtzia, Endostemon, Englerastrum, Eremostachys, Eriope, Eriophyton, Eriopidion, Eriothymus, Erythrochlamys, Euhesperida, Eurysolen, Faradaya, Fuerstia, Galeopsis, Garrettia, Geniosporum, Glechoma, Glechon, Glossocarya, Gmelina, Gomphostemma, Gontscharovia, Hanceola, Haplostachys, Haumaniastrum, Hedeoma, Hemiandra, Hemigenia, Hemiphora, Hemizygia, Hesperozygis, Heterolamium, Hoehnea, Holmskioldia, Holocheila, Holostylon, Horminum, Hosea, Hoslundia, Huxleya, Hymenocrater, Hymenopyramis, Hypenia, Hypogomphia, Hyptidendron, Hyptis, Hyssopus, Isodictyophorus, Isodon, Isoleucas, Kalaharia, Karomia, Keiskea, Killickia, Kudrjaschevia, Kurzamra, Lachnostachys, Lagochilus, Lagopsis, Lallemantia, Lamiophlomis, Lamium, Lavandula, Leocus, Leonotis, Leonurus, Lepechinia, Leucas, Leucophae, Leucosceptrum, Limniboza, Lophanthus, Loxocalyx, Lycopus, Macbridea, Madlabium, Mallophora, Marmoritis, Marrubium, Marsypianthes, Matsumurella, Meehania, Melissa, Melittis, Mentha, Meriandra, Mesona, Metastachydium, Microcorys, Micromeria, Microtoena, Minthostachys, Moluccella, Monarda, Monardella, Monochilus, Mosla, Neoeplingia, Neohyptis, Neorapinia, Nepeta, New castelia, Nosema, Notochaete, Obtegomeria, Ocimum, Octomeron, Ombrocharis, Oncinocalyx, Origanum, Orthosiphon, Otostegia, Ovieda, Oxera, Panzerina, Paralamium, Paraphlomis, Paravitex, Peltodon, Pentapleura, Perilla, Perillula, Peronema, Perovskia, Perrierastrum, Petitia, Petraeovitex, Phlomidoschema, Phlomis, Phlomoides, Phyllostegia, Physopsis, Physostegia, Piloblephis, Pitardia, Pityrodia, Platostoma, Plectranthus, Pogogyne, Pogostemon, Poliomintha, Prasium, Premna, Prostanthera, Prunella, Pseuderemostachys, Pseudocarpidium, Pseudocaryopteris, Pseudomarrubium, Puntia, Pycnanthemum, Pycnostachys, Rabdosiella, Renschia, Rhabdocaulon, Rhaphiodon, Rhododon, Rosmarinus, Rostrinucula, Rotheca, Roylea, Rubiteucris, Rydingia, Sabaudia, Saccocalyx, Salazaria, Salvia, Satureja, Schizonepeta, Schnabelia, Scutellaria, Sideritis, Siphocranion, Solenostemon, Spartothamnella, Sphenodesme, Stachydeoma, Stachyopsis, Stachys, Stenogyne, Sulaimania, Suzukia, Symphorema, Symphostemon, Synandra, Syncolostemon, Tectona, Teijsmanniodendron, Tetraclea, Tetradenia, Teucridium, Teucrium, Thorncroftia, Thuspeinanta, Thymbra, Thymus, Tinnea, Trichostema, Tripora, Tsoongia, Vitex, Viticipremna, Volkameria, Warnockia, Wenchengia, Westringia, Wiedemannia, Wrixonia, Xenopoma, Zataria, Zhumeria* and *Ziziphora*.

In various embodiments, the extract is from *Melissa officinalis*.

The methods disclosed herein can be used against any filovirus. In one embodiment, the filovirus is an Ebola virus. In another embodiment, the filovirus is a Marburg virus.

In various embodiments in which the methods are used to treat or prevent viral infection of a cell, the cell can be a human cell.

In various embodiments of the methods disclosed herein, the extract of *Melissa officinalis* comprises dried plant material and extraction solution. In other embodiments, the extract of *Melissa officinalis* comprises fresh plant material and extraction solution.

The extraction solution present in the extract of *Melissa officinalis* comprises water and glycerin. In various embodiments, the extraction solution comprises glycerin in an amount ranging from about 0.01% to about 90%, from about 50% to about 85%, or from about 65% to about 80%.

In various embodiments, the extraction solution further comprises ethanol. In various embodiments, the extraction solution comprises ethanol in an amount ranging from about 0.01% to about 30%, from about 10% to about 25%, or from about 15% to about 20%.

In one embodiment, the *Melissa officinalis* extract comprises dried plant material and extraction solution and the ratio between the dried plant material and the extraction solution is from about 1:3 to about 1:15, from about 1:6 to about 1:12 or from about 1:7 to about 1.10.

In another embodiment, the *Melissa officinalis* extract comprises fresh plant material and extraction solution and the ratio between the fresh plant material and the extraction solution is from about 1:3 to about 1:15, from about 1:6 to about 1:12, or from about 1.7 to about 1.10.

In certain embodiments, the method of treating a subject infected with a filovirus further comprises administering a second therapeutic agent. The second therapeutic agent includes those that are known and those discovered to be effective in the treatment of filovirus viral infections or effective in ameliorating or alleviating symptoms associated with filovirus viral infections. The extracts herein and the second therapeutic agent may be administered simultaneously in either the same or different composition or sequentially in any order. The amounts of extract described herein and the second therapeutic agent and the relative timings of their administration will be selected to achieve the desired combined effect.

Any extract described herein may be used in the methods of the present disclosure.

In preferred embodiments of each of the above methods, the subject is a human.

In order that this invention be more fully understood, the following examples are set forth. These examples are for the purpose of illustration only, are applicable to one or more embodiments and are not to be construed as limiting the scope of the invention in any way.

EXAMPLES

Figure 6:
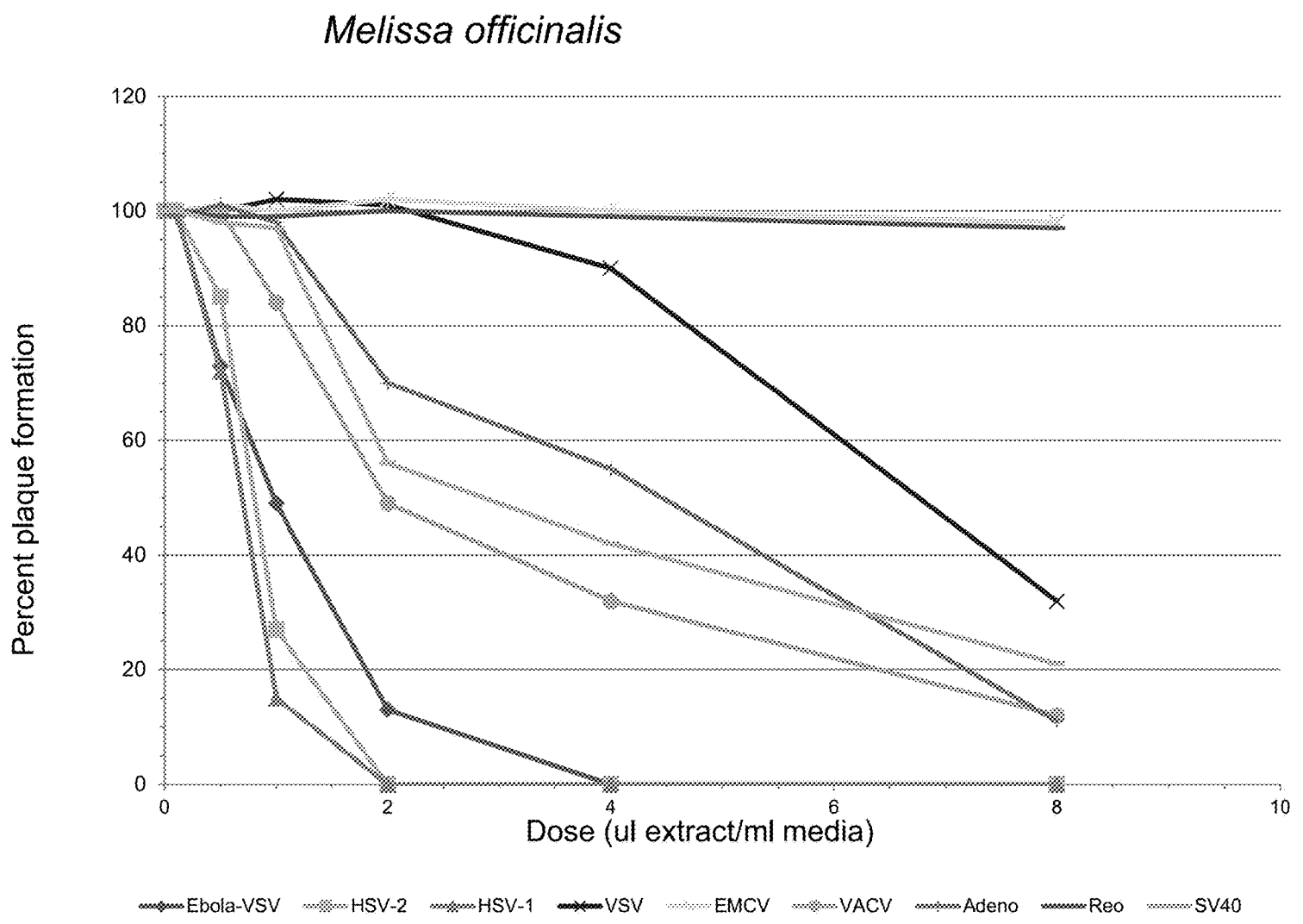
Figure 7:
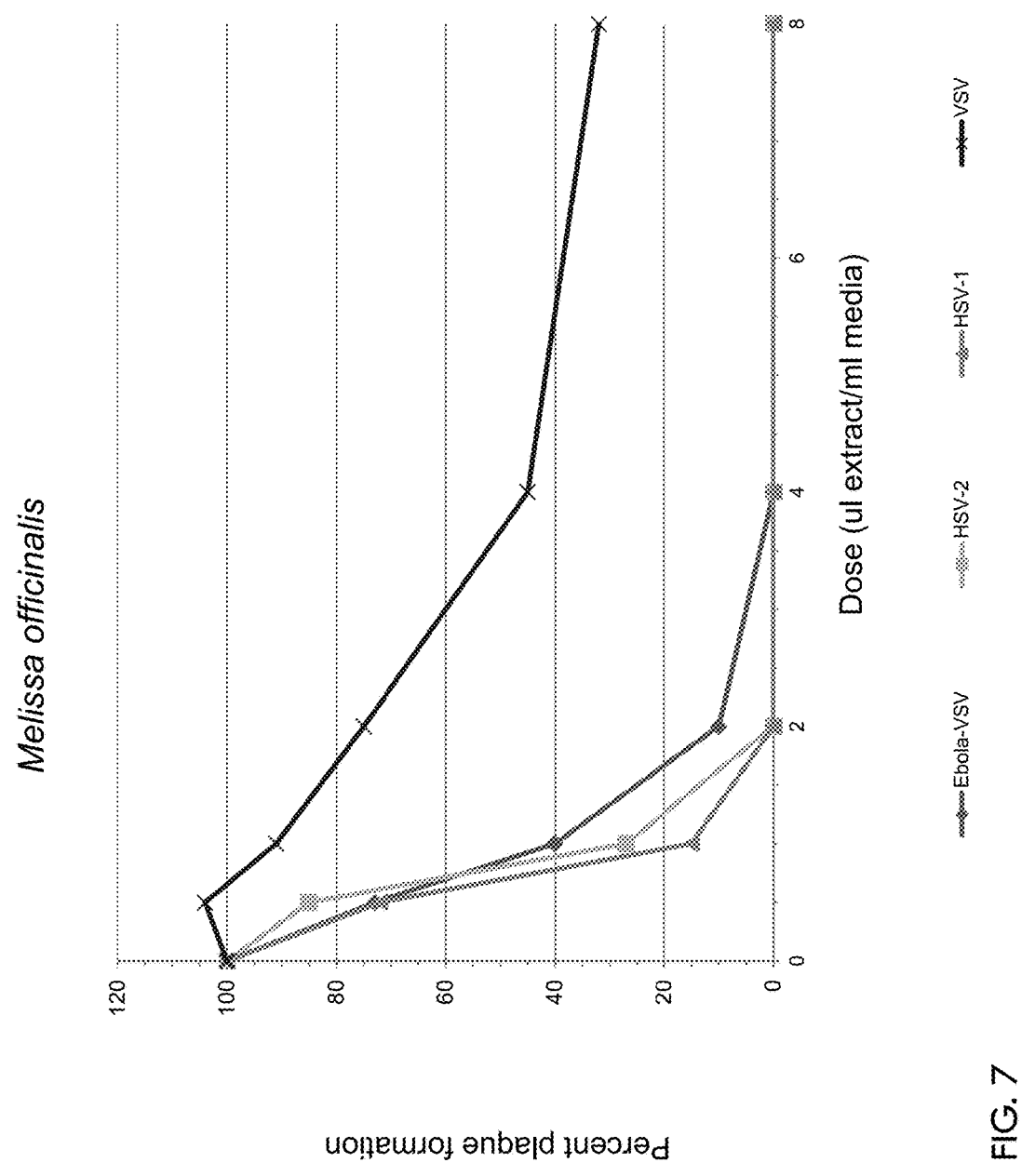

When the Melissa extract was tested against a variety of viruses, including the ebola chimera (ebola-VSV) and parental VSV, the extract dramatically inhibited the ebola-VSV chimera to levels similar to HSV1 and HSV2 (FIG. 6). However, the parental VSV and as well as several other viruses (including vaccinia virus, SV40, adenovirus, reovirus and encephalomyocarditis virus) were poorly or not inhibited by the Melissa extract (FIG. 6). These results suggest that the Melissa extract is capable of inhibiting ebola virus infection of cells to a similar level of that observed with herpes viruses. This experiment was repeated with a separately prepared extraction of Melissa and as shown in FIG. 7, plaque formation with the ebola-VSV chimera was strongly inhibited whereas the parental VSV virus required a much higher dose for inhibition. Since the only difference between the ebola-VSV chimera and the parental VSV are the viral surface glycoproteins, these results support that components present in the Melissa extract are likely interacting with the ebola surface GP and blocking its interaction with the cellular heparin sulfate proteoglycans by a similar mechanism to that observed with HSV1.

Figures 8A, 8B:
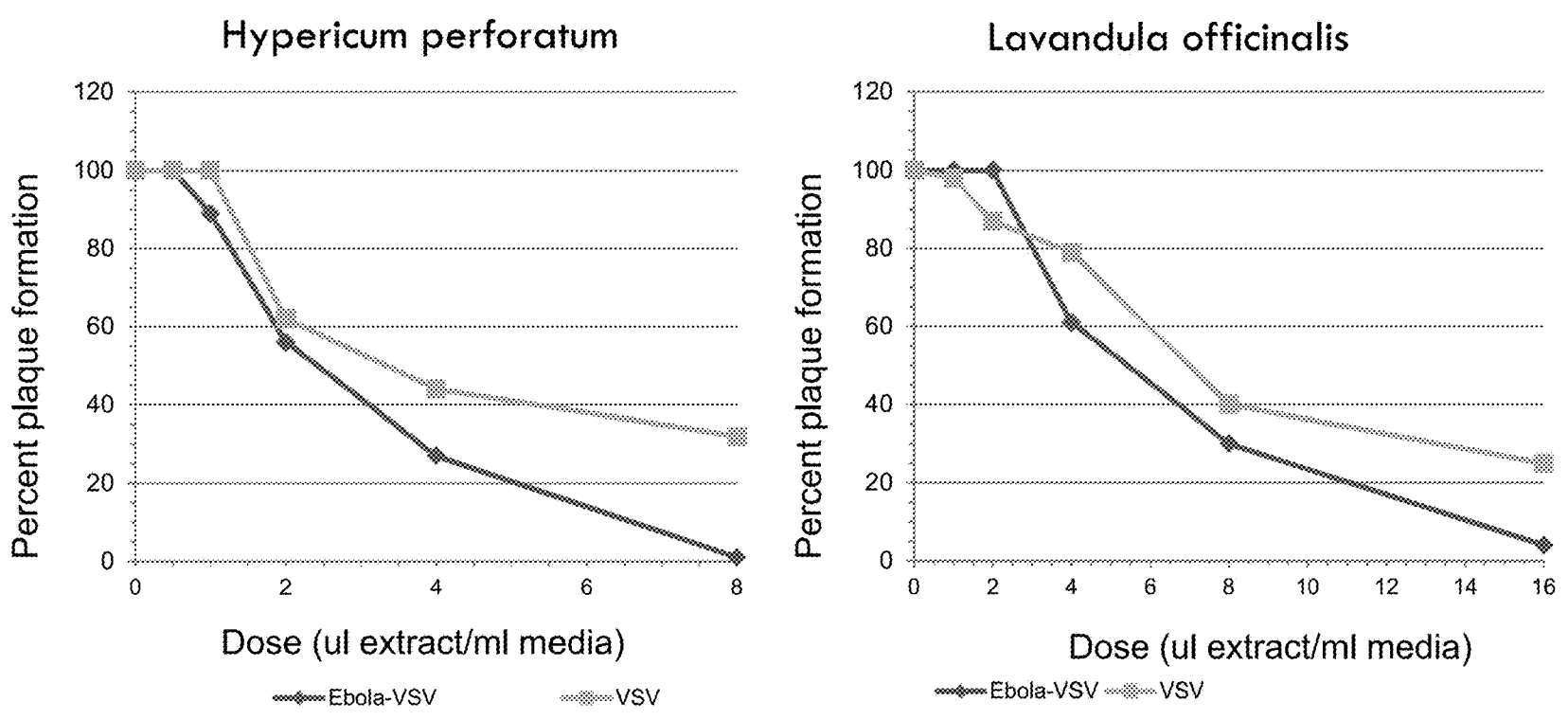

To confirm specificity associated with the botanical *Melissa officinalis*, two other botanicals which inhibit HSV1 were tested for their ability to inhibit replication of the ebola-VSV chimera and the parental VSV. As shown in FIG. 8, the botanicals *Hypericum perforatum* and *Lavandula officinalis* were able to inhibit the replication of both the ebola-VSV chimera and the parental VSV with similar growth reduction curves. This suggests that these botanicals are likely acting on a target present in VSV and therefore was equally able to inhibit both viruses. This again supports the specificity of the Melissa extract in targeting interaction of the ebola surface GP with the cell receptor, heparin sulfate proteoglycans.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed:

1. A method of inhibiting viral replication of a filovirus, the method comprising exposing the filovirus or a filovirus-infected cell to an effective amount of an extract from *Melissa officinalis*, or a composition comprising the extract, wherein the exposing inhibits viral replication within the cell.

2. A method of treating filovirus infection of a cell, the method comprising exposing a filovirus or filovirus-infected cell to an effective amount of an extract from *Melissa officinalis*, or a composition comprising the extract, wherein the exposing inhibits the entry of the filovirus into the cell.

3. A method of preventing filovirus infection of a cell, the method comprising exposing the cell to an effective amount of an extract from *Melissa officinalis*, or a composition comprising the extract, prior to exposure of the cell to the filovirus, wherein the exposing the cell to the *Melissa officinalis* extract, or a composition comprising *Melissa officinalis* extract inhibits filovirus infection.

4. A method of treating a subject infected with filovirus, the method comprising administering an effective amount of an extract from *Melissa officinalis*, or a composition comprising the extract, to the subject, thereby treating the subject infected with filovirus.

5. A method of preventing infection of a subject with filovirus, the method comprising administering an effective amount of an extract from *Melissa officinalis*, or a composition comprising the extract, to the subject prior to exposure of the subject to filovirus, thereby preventing infection with filovirus.

6. The method of claim 4, wherein the filovirus is an Ebola virus.

7. The method of claim 4, wherein the filovirus is Marburg virus.

8. The method of claim 5, wherein the filovirus is an Ebola virus.

9. The method of claim 5, wherein the filovirus is Marburg virus.

10. The method of claim 1, wherein the cell is a human cell.

11. The method of claim 1, wherein the filovirus is an Ebola virus.

12. The method of claim 1, wherein the filovirus is Marburg virus.

13. The method of claim 1, wherein the extract comprises dried plant material and extraction solution.

14. The method of claim 1, wherein the extract comprises fresh plant material and extraction solution.

15. The method of claim 13, wherein the extraction solution comprises water.

16. The method of claim 15, wherein the extraction solution further comprises glycerin.

17. The method of claim 16, wherein the extraction solution comprises glycerin in an amount ranging from about 0.01% to about 90%.

18. The method of claim 15, wherein the extraction solution further comprises ethanol.

19. The method of claim 18, wherein the extraction solution comprises ethanol in an amount ranging from about 0.01% to about 30%.

\* \* \* \* \*